United States Patent
Branlard et al.

(10) Patent No.: US 6,395,704 B1
(45) Date of Patent: May 28, 2002

(54) PERFUME COMPOSITION USING ORGANOPOLYSILOXANES

(75) Inventors: Paul Branlard; Gérard Mignani, both of Lyons; Claudie Willemin, Paris; Philippe Olier, Lyons, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/463,678

(22) PCT Filed: Jul. 30, 1998

(86) PCT No.: PCT/FR98/01699

§ 371 (c)(1), (2), (4) Date: Apr. 21, 2000

(87) PCT Pub. No.: WO99/06017

PCT Pub. Date: Feb. 11, 1999

(30) Foreign Application Priority Data

Jul. 31, 1997 (FR) .............................................. 97 09812
Apr. 9, 1998 (FR) .............................................. 98 04483

(51) Int. Cl.⁷ .............................. A61K 7/00; A61K 7/46
(52) U.S. Cl. ............................. 512/1; 424/401; 512/2
(58) Field of Search ............................. 424/401; 512/1, 512/2

(56) References Cited

U.S. PATENT DOCUMENTS

| 5,008,101 A | * | 4/1991 | Klimisch et al. | .............. 424/59 |
| 5,460,804 A | * | 10/1995 | Krzysik | ....................... 424/60 |
| 5,492,691 A | * | 2/1996 | Bahr et al. | ..................... 404/65 |
| 5,585,343 A | * | 12/1996 | McGee et al. | .................. 512/1 |
| 6,083,900 A | * | 7/2000 | Auguste et al. | ................. 512/2 |

FOREIGN PATENT DOCUMENTS

JP  07089844  * 4/1995

* cited by examiner

*Primary Examiner*—Jose' G. Dees
*Assistant Examiner*—Marina Lamm

(57) ABSTRACT

The invention concerns a perfume composition comprising a perfume base and a lipophilic solubilizing agent based on at least an organopolysiloxane having according to Hansen solubility parameter the following characteristics: $\delta_D$ London interactions ranging from (8) to (21) $(J/cm^3)^{1/2}$, $\delta_P$ of Keesom interactions greater than 0 and capable of reaching 25 $(J/cm^3)^{1/2}$, $\delta_H$ of hydrogen binding ranging from (0) to (23) $(J/cm^3)^{1/2}$. Said organotrisiloxanes with polar or polarizsable function of formula (I) are used as solubilizing agents and emollients in perfume composition.

20 Claims, No Drawings

PERFUME COMPOSITION USING ORGANOPOLYSILOXANES

This application is an application under 35 U.S.C. Section 371 of International Application Number PCT/FR98/01699, filed on Jul. 30, 1998.

The present invention relates to a fragrance composition comprising a fragrance base and a lipophilic solubilizing agent based on at least one polyorganosiloxane containing a polar or polarizable function; the invention also relates to the use of polyorganosiloxanes containing a polar or polarizable function as agents for dissolving fragrance bases and emollients in fragrance compositions.

A first subject of the invention consists of a fragrance composition comprising a fragrance base and a lipophilic agent for dissolving the said fragrance base, the said solubilizing agent being based on at least one linear polyorganosiloxane containing a polar or polarizable function of formula (I)

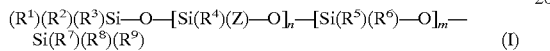

(R$^1$)(R$^2$)(R$^3$)Si—O—[Si(R$^4$)(Z)—O]$_n$—[Si(R$^5$)(R$^6$)—O]$_m$—Si(R$^7$)(R$^8$)(R$^9$)     (I)

or a cyclic polyorganosiloxane of formula (I')

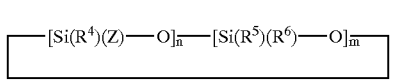

—[Si(R$^4$)(Z)—O]$_{\overline{n}}$—[Si(R$^5$)(R$^6$)—O]$_{\overline{m}}$—     (I')

in which formula (I)
the symbols R$^1$ and R$^9$ are identical or different and represent the symbol Z or an alkyl radical containing from 1 to 8 carbon atoms, preferably 1 or 2 carbon atoms, most particularly 1 carbon atom
the symbols R$^2$, R$^3$, R$^4$, R$^5$, R$^6$, R$^7$ and R$^8$ are identical or different and represent an alkyl radical containing from 1 to 8 carbon atoms, preferably 1 or 2 carbon atoms, most particularly 1 carbon atom
the symbol Z represents a polar or polarizable organic radical
n is an integer or decimal number which can range from 0 to 5, preferably equal to 0 or 1,
at least one of the radicals R$^1$ and R$^9$ representing the symbol Z when n is equal to 0
m is an integer or decimal number which can range from 0 to 5, preferably equal to 0
formula (I') in which
the symbols R$^4$, R$^5$, R$^6$ and Z have the same definition as that given above
n is an integer or decimal number which can range from 1 to 5, preferably equal to 1
m is an integer or decimal number which can range from 1 to 5, with n+m at least equal to 3,
the said polyorganosiloxane having the following Hansen solubility parameters
  δ$_D$ of London interactions ranging from 8 to 21 (J/cm$^3$)$^{1/2}$
  δ$_P$ of Keesom interactions of greater than 0 and possibly ranging up to 25 (J/cm$^3$)$^{1/2}$
  δ$_H$ of hydrogen bonding ranging from 0 to 23 (J/cm$^3$)$^{1/2}$.

The three-dimensional solubility space, in which the solvents and all the organic molecules exist, is defined by C M Hansen in "The three dimensional solubility parameters" J. Paint Technol. 39, 105 (1967); δ$_D$, δ$_P$ and δ$_H$ represent the partial solubility parameters associated, respectively, with the London dispersion forces, the Keesom polarity forces and the hydrogen bonding forces, given that these partial parameters are the components of the overall solubility parameter δ, referred to as the Hildebrand solubility parameter, associated with the voluminal cohesion of the molecule.

Examples of polar organic radicals Z which may be mentioned are
  ester groups of formulae —R'OOC—R" and —R'—COOR'" directly linked to silicon, in which formulae
    R' represents a saturated or unsaturated, linear or branched aliphatic multivalent group containing from 2 to 10 carbon atoms
    R" represents a C$_1$–C$_8$, preferably C$_1$–C$_3$, alkyl group
    R'" represents a C$_1$–C$_5$, preferably C$_1$–C$_3$, alkyl group
  the hydroxyl or alcohol groups of formula —R'—O—(RO)$_x$H directly linked to silicon, in which formula
    R' represents a saturated or unsaturated, linear or branched aliphatic multivalent group containing from 2 to 10 carbon atoms
    R represents a linear or branched alkylene group, which may be identical or different, containing 2 or 3 carbon atoms
    x can range from 0 to 20
  primary or secondary amido groups —R'—CO—NH(R), directly linked-to silicon, in which R' represents a saturated or unsaturated, linear or branched aliphatic multivalent group containing from 2 to 10 carbon atoms
  carboxyl groups —R'—COOH, directly linked to silicon, in which R' represents a saturated or unsaturated, linear or branched aliphatic multivalent group containing from 2 to 10 carbon atoms
  linear or branched, saturated or unsaturated, C$_6$–C$_{20}$ haloaliphatic radicals, in particular chloro- or fluoroaliphatic radicals
  saturated or unsaturated, C$_5$–C$_6$ halocycloaliphatic radicals, in particular chloro- or fluorocycloaliphatic radicals, directly linked to silicon via a saturated or unsaturated, linear or branched aliphatic multivalent group containing from 2 to 10 carbon atoms
  aryl radicals, preferably C$_6$ aryl radicals, substituted with at least one halogen atom (in particular chlorine or fluorine), directly linked to silicon via a saturated or unsaturated, linear or branched aliphatic multivalent group containing from 2 to 10 carbon atoms.

Mention may be made more particularly of 3-propylol, 2-propyloxyethanol, diethyl 3-propyl malonate and ethylpyrrolidone radicals, which radicals can be obtained by opening the vinylic double bond of, respectively, allyl alcohol, allyloxyethanol, diethyl allyl malonate or vinylpyrrolidone, as well as 3-propylacetate.

Examples of polarizable organic radicals Z which may be mentioned are
  linear or branched C$_6$–C$_{20}$ aliphatic radicals containing at least one internal ethylenic unsaturation, preferably two conjugated double bonds
  ethylenically unsaturated C$_5$–C$_6$ cycloaliphatic radicals, optionally substituted with at least one C$_1$–C$_8$ alkyl group, linked directly to silicon via a saturated or unsaturated, linear or branched aliphatic multivalent group containing from 2 to 10 carbon atoms
  a phenyl radical
  aryl radicals, preferably C$_6$ aryl radicals, optionally substituted with at least one C$_1$–C$_8$ alkyl or C$_6$ aryl group, linked directly to silicon via a saturated or unsaturated, linear or branched aliphatic multivalent group containing from 2 to 10 carbon atoms.

Mention may be made more particularly of a phenyl radical and the radicals obtained by opening the vinylic double bond of styrene, of α-methylstyrene, of α-methylstyrene dimer, of dihydromyrcene, of limonene, etc., or the terminal triple bond of phenylacetylene, etc.

The said radical Z is preferably a phenyl radical, a phenylalkyl radical in which the alkyl residue contains from 2 to 10 carbon atoms, or a phenylalkenyl radical in which the alkenyl residue contains from 2 to 10 carbon atoms, in particular phenyl(methyl)methyl, phenylethenyl and, most particularly, phenylethyl. Most preferably, the fragrance composition comprises a mixture of polyorganosiloxanes predominantly containing a polyorganosiloxane containing a phenylethyl radical, a smaller amount of a polyorganosiloxane containing a phenyl(methyl)methyl radical and a small amount of a polyorganosiloxane containing a phenylethenyl radical.

Preferably, the said polyorganosiloxane is a organodisiloxane MM of formula (I) in which n and m are equal to 0 and $R^1$ and $R^9$ represent a phenyl radical, in particular diphenyltetramethyldisiloxane, or a linear organotrisiloxane MDM of formula (I) in which n is equal to 1 and m is equal to 0, the symbols $R^1$, $R^2$, $R^3$, $R^4$, $R^7$, $R^8$ and $R^9$ preferably being methyl radicals.

The said polyorganosiloxanes of formula (I) or (I') in which the polar or polarizable function (Z) is other than phenyl can be obtained in a known manner by hydrosilylation between at least one hydrogenopolyorganosiloxane of formula (II) or (II')

$$(R^1)(R^2)(R^3)Si\text{—}O\text{—}[Si(R^4)(H)\text{—}O]_n\text{—}[Si(R^5)(R^6)\text{—}O]_m\text{—}Si(R^7)(R^8)(R^9) \quad (II)$$

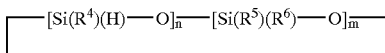
(II')

in which formulae the symbols $R^1$, $R^2$, $R^3$, $R^4$, $R^5$, $R^6$, $R^7$, $R^8$, $R^9$, n and m have the same definition as that given above, and the compound containing vinylic or terminal acetylenic unsaturation from which the radical Z is derived, in the presence of a hydrosilylation catalyst, in particular such as platinum.

This operation can be carried out with a slight excess of one or other of the reagents, generally up to 10 mol % relative to the stoichiometry, at a temperature of about 50° C. to 100° C., preferably from about 50° C. to 80° C., in the presence of 5 to 50 parts by mass of platinum (for example Karstedt catalyst) per million parts by mass of monomers used.

The hydrogenopolyorganosiloxanes preferably used are hydrogenoheptaorganotrisiloxanes MD'M, particularly hydrogenoheptamethyltrisiloxane.

Among the compounds containing vinylic or terminal acetylenic unsaturation which can preferably be used, mention may be made of allyl alcohol, allyloxyethanol, diethyl allyl malonate, styrene, α-methylstyrene, α-methylstyrene dimer, dihydromyrcene, limonene, vinylpyrrolidone and phenylacetylene. The said compound is most preferably styrene.

One specific embodiment of the first subject of the invention consists of a fragrance composition comprising a fragrance base and a lipophilic agent for dissolving the said fragrance base, the said solubilizing agent being based on phenylethylheptamethyltrisiloxane in particular based on a mixture of heptamethyltrisiloxanes containing polymerizable functions consisting for more than 70% by mass, generally for at least 75% by mass, of phenylethylheptamethyltrisiloxane of formula

in which $Z^1$ represents the —$CH_2$—$CH_2$—Ph function for less than 25% by mass, generally from 10 to 20% by mass, of trisiloxane of formula

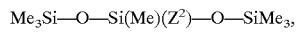

in which $Z^2$ represents the —$CH(CH_3)$—Ph function and less than 5% by mass, generally from 0 to 2% by mass, of trisiloxane of formula

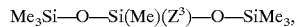

in which $Z^3$ represents the —CH=CH—Ph function in which formulae Me represents a methyl radical and Ph represents a phenyl radical.

The said mixture can be obtained by hydrosilylation reaction at a temperature of from 50 to 150° C., preferably from 50 to 100° C., most particularly from 60 to 90° C., of hydrogenoheptamethyltrisiloxane (reagent SiH) and of styrene (reagent Vi), in the presence of hexamethyldisiloxane as solvent. This hydrosilylation operation is carried out by simultaneously introducing the two reagents (Vi) and (SiH) into the reaction medium comprising the solvent and a hydrosilylation catalyst, this introduction being carried out such that the respective amounts of the two reagents (Vi) and (SiH) correspond to a reagent (Vi)/reagent (SiH) molar ratio of from more than 0.5 to 1.5, preferably of from more than 1 to 1.2, and that, at any moment in the hydrosilylation reaction, the amount of reagent (SiH) present, expressed as mass of SiH functions (29 g per 1 function), corresponds to less than 2%, preferably less than 1% of the reaction mass, excluding the mass of solvent. In the definition of a mole of hydrogenoheptamethyltrisiloxane, reagent (SiH), the —SiH function is considered as being the elemental species. In the definition of a mole of styrene, reagent (Vi), a gram-molecule of styrene is considered as being the elemental species. Karstedt hydrosilylation catalyst is used, for example, in a proportion of from 1 to 300 parts, preferably from 5 to 100 parts, by mass of platinum per million parts by mass of reagents (SiH) and (Vi) used. The hydrosilylation operation is preferably carried out under atmospheric pressure. The introduction of the reagents (SiH) and (Vi) is preferably carried out by simultaneously adding the two reagents continuously to the reaction mass comprising the solvent and the catalyst. The duration of the additions is adjusted such that the reagent (Vi) is consumed by hydrosilylation as it is introduced. The solvent and the unreacted reagents are then removed. Their removal can be carried out by distillation under vacuum or under reduced pressure (for example about 1.013 Pa to 101,300 Pa). This distillation operation is followed by a hydrogenation operation. This can be carried out at a temperature from about 25 to 200° C., preferably from about 50 to 150° C., at a hydrogen pressure from about 0 to 50 bar, preferably from about 5 to 25 bar, in the presence of a hydrogenation catalyst such as platinum or palladium, in an amount of from 0.01 to 5%, preferably from 0.01 to 1%, by weight of metal relative to the mass to be hydrogenated. The medium is then optionally subjected to an operation to remove the products other than the heptamethyltrisiloxanes containing polarizable functions. This removal operation can be carried out by distillation under vacuum or reduced pressure, for example a pressure from about 1.013 Pa to 101,300 Pa.

The fragrance composition which forms the subject of the invention can comprise from about 3 to 20% of its weight of a fragrance base, and 75 to 97% of its weight of a lipophilic solubilizing agent based on at least one of the polyorganosiloxanes containing a polar or polarizable function of formula (I) or (I').

The fragrance base present can be any compound used in the perfume industry and responsible for various perfume notes. A distinction is made among hesperidic fresh notes, eaux de cologne and fresh waters; among floral notes, simple, flowery, green flowery and aldehydic flowery types; among fern notes, amber or aromatic fern; among oriental notes, spiced oriental and flowery amber types; among chyphre notes, fruity chyphre, aldehydic flowery chyphre, green chyphre and leathery chyphre types.

As examples of chemical compounds which can form part of the composition of the said fragrance base, mention may be made, in a non-limiting manner, of acetophenone, methylacetophenone, cinnamic aldehyde, amylcinnamic aldehyde, lanlsic aldehyde, cuminic aldehyde, cyclamen aldehyde, hydratropic aldehyde, p-cresyl methyl ether, benzophenone, citral, citronellyl oxyacetaldehyde, allyl hexanoate, amyl hexanoate, cinnamyl isobutyrate, geranyl acetate or phenyl acetate, linalyl acetate, menthyl acetate, phenylethyl acetate, vetiveryl acetate, jasmyl acetate, phenylethyl formate, ethylmethylphenyl glycidate, eugenol, isoeugenol, geraniol, citronellal, hydroxycitronellal, ionone, methylionone, phenylacetaldehyde dimethyl acetal, menthol, musk, phenylethyl alcohol, pinene derivatives, camphene derivatives, carvone, cinnamyl alcohol, coumarin, dimethylbenzylcarbinyl acetate, heliotropin, isocyclocitral, methylnonyl acetaldehyde, undecalactone, vanillin, etc. taken together or as mixtures with each other.

The fragrance composition forming the subject of the invention is a solution.

The solubilizing agent present can consist of at least one of the polyorganosiloxanes, in particular organodisiloxanes and organotrisiloxanes, containing a polar or polarizable function of formula (I) or (I').

According to one embodiment, the said solubilizing agent consists of at least one of the polyorganosiloxanes, in particular organodisiloxanes and organotrisiloxanes, containing a polar or polarizable function of formula (I) or (I'), combined with at least one other volatile or non-volatile solvent for fragrance bases, such as volatile silicones (for example hexamethyldisiloxane, decamethylcyclopentasiloxane, linear volatile polydimethylsiloxanes, linear or cyclic volatile alkylpolymethylsiloxanes in which the alkyl radical contains from 2 to 13 carbon atoms, described in U.S. Pat. No. 5,160 494, ethanol, propylene glycol and esters (for example diethylene glycol dioctanoate or diisononanoate).

The said other solvent(s) can be present in a polyorganosiloxane(s) containing a polar or polarizable function of formula (I) or (I')/other solvent(s) weight ratio from about 5/95 to 95/5, preferably from about 10/90 to 90/10, most particularly from about 25/75 to 90/10.

Most preferably, the said solubilizing agent consists:

of phenylethylheptamethyltrisiloxane (PEHMTS) or of a mixture (M) consisting for more than 70% by mass, generally for at least 75% by mass, of phenylethylheptamethyltrisiloxane of formula

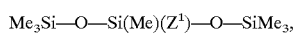

in which $Z^1$ represents the —$CH_2$—$CH_2$—Ph function for less than 25% by mass, generally from 10 to 20% by mass, of trisiloxane of formula

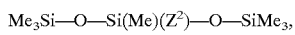

in which $Z^2$ represents the —$CH(CH_3)$—Ph function and less than 5% by mass, generally from 0 to 2% by mass, of trisiloxane of formula

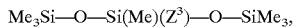

in which $Z^3$ represents the —CH=CH—Ph function in which formulae Me represents a methyl radical and Ph represents a phenyl radical, the said phenylethylheptamethyltrisiloxane or the said mixture (M) possibly being alone or combined with a volatile silicone solvent, in particular hexamethyldisiloxane, and/or ethanol, in a (PEHMTS)/hexamethyldisiloxane and/or ethanol, or mixture (M)/hexamethyldisiloxane and/or ethanol, weight ratio from about 5/95 to 95/5, preferably from about 10/90 to 90/10, most particularly from about 25/75 to 90/10.

This combination makes it possible to prepare fragrance compositions from fragrance bases of very diverse polarities, in particular as diverse as those of coumarin, vanillin, acetophenone and lavender, these fragrance bases having the following Hansen solubility parameters:

| | lavender | acetophenone | vanillin | coumarin |
|---|---|---|---|---|
| $\delta_D$ $(J/cm^3)^{1/2}$ | 17.1 | 19.6 | 16.6 | 19.25 |
| $\delta_P$ $(J/cm^3)^{1/2}$ | 7.6 | 8.6 | 12.1 | 12.2 |
| $\delta_H$ $(J/cm^3)^{1/2}$ | 7.6 | 3.7 | 12 | 6.8 |

The polyorganosiloxanes containing a polar or polarizable function of formula (I) or (I') also give the fragrance composition forming the subject of the invention sensory properties (in particular a dry feel without residue).

The fragrance composition forming the subject of the invention can also comprise up to 5% of its weight of other constituents, such as preserving agents, light-stabilizers, oxygen-stabilizers, dyes, refreshing agents such as menthyl lactate and menthone glycerol acetal, moisturizers, preserving agents, etc.

The fragrance composition forming the subject of the invention is present in the form of a solution; it can be used as an alcohol-free fragrance or a fragrance containing a small amount of alcohol (as it is or on a textile support or the like) or as an additive for fragrancing cosmetic formulations (care creams, deodorants, antiperspirants, shaving products, etc.).

A second subject of the invention consists of the use, in fragrance compositions comprising a fragrance base, of polyorganosiloxanes containing a polar or polarizable function of formula (I) or (I') as agents for dissolving the said fragrance base.

The present invention is also directed towards the use, in fragrance compositions comprising a fragrance base, of polyorganosiloxanes containing a polar or polarizable function of formula (I) or (I') as emollients (providing sensory properties).

A third subject of the invention consists of a process for preparing a liquid fragrance composition containing a fragrance base, by dissolving the said fragrance base using at least one of the polyorganosiloxanes containing a polar or polarizable function of formula (I) or (I').

The present invention is also directed towards a process for giving sensory properties to a liquid fragrance composition containing a fragrance base, by dissolving the said fragrance base using at least one of the polyorganosiloxanes containing a polar or polarizable function of formula (I) or (I').

The polyorganosiloxanes containing a polar or polarizable function of formula (I) or (I') which are preferred, the amounts of the said polyorganosiloxanes used, and those of the fragrance base and of the other solvents or additives optionally present, have already been mentioned above.

The examples which follow are given without any limitation being implied.

EXAMPLE 1

Hydrosilylation of Styrene with Heptamethyltrisiloxane 1803 g (11.12 mol) of hexamethyldisiloxane (HMDS) and 4.15 g of a Karstedt platinum solution with a titre of 11.5% platinum(0) are introduced, using a pump, into a 10-liter reactor. The reaction mass is brought to 90° C. and 4150 g (19.3 mol) of heptamethyltrisiloxane (MD'M) and 2207 g (21.22 mol) of styrene are simultaneously added over 5 hours.

Monitoring of the major species by gas chromatography shows that the reaction is virtually quantitative (in % by weight).

| time | HMDS | styrene | MD'M | X-HMTS | Y-HMTS | Z-HMTS |
|------|------|---------|------|--------|--------|--------|
| 1 h  | 54.9 | 0.6     | 1.5  | 30.4   | 0.8    | 5.6    |
| 2 h  | 36.9 | 2.0     | 1.6  | 42.9   | 1.7    | 7.8    |
| 3 h  | 30.3 | 2.3     | 2.1  | 47.7   | 2.5    | 8.3    |
| 4 h  | 24.2 | 2.1     | 2.8  | 53.2   | 3.2    | 9.3    |
| 5 h  | 21.7 | 3.2     | 2.5  | 53.2   | 3.3    | 9.3    |

The content of free styrene in the reaction mass, at the end of the reaction, represents 88% of the excess styrene used, which is proof of a very poor polymerization. The remainder to 100% consists of the product of reaction of the MD'M side products (in particular MD'DM and MM') and of styrene.

In this table,
X-HMTS has the following meaning

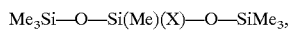
Me$_3$Si—O—Si(Me)(X)—O—SiMe$_3$, in which X represents the —CH$_2$—CH$_2$—Ph function
Y-HMTS has the following meaning

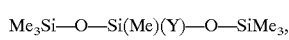
Me$_3$Si—O—Si(Me)(Y)—O—SiMe$_3$, in which Y represents the —CH=CH—Ph function
Z-HMTS has the following meaning

Me$_3$Si—O—Si(Me)(Z)—O—SiMe$_3$, in which Z represents the —CH(CH$_3$)—Ph function with Me representing methyl and Ph representing phenyl.

Distillation

The reaction mass is then concentrated (evaporation of the volatiles at 110° C. under 20 mbar for 7 hours). 5827 g of a coloured product with the composition below are collected (values in % by weight):

| HMDS | styrene | MD'M | X-HMTS | Y-HMTS | Z-HMTS |
|------|---------|------|--------|--------|--------|
| 0.13 | 0.13    | 0.12 | 77.8   | 4.9    | 14.6   |

Hydrogenation 700 g of this coloured product are loaded into a 1 liter autoclave reactor.

14 g (i.e. 2% by weight) of a platinum catalyst on charcoal, with a Pt titre of 2% are introduced. The-reaction mass is brought to 100° C. under a pressure of 20 bar of hydrogen. After reaction for 3 hours with stirring, the reaction mass is cooled and returned to atmospheric pressure. After filtration, 692 g of a colourless product of the composition below are obtained:

| HMDS | styrene | MD'M | X-HMTS | Y-HMTS | Z-HMTS |
|------|---------|------|--------|--------|--------|
| 0.13 | 0       | 0.1  | 80.75  | 1.10   | 14.3   |

After distillation on a column packed with Rashig rings (height=40 cm), 563.3 g (yield=81.4%) of a mixture (M) of the composition below are collected:

| HMDS | styrene | MD'M | X-HMTS | Y-HMTS | Z-HMTS |
|------|---------|------|--------|--------|--------|
| 0    | 0       | 0    | 81.5   | 1.04   | 16.6   |

EXAMPLE 2

The fragrance base used is lavender, the essential oil from the company Firmenich, which has the following solubility parameters $\delta_D$ of 17.1 (J/cm$^3$)$^{1/2}$ $\delta_P$ of 7.6 (J/cm$^3$)$^{1/2}$ $\delta_H$ of 7.6 (J/cm$^3$)$^{1/2}$ The lipophilic solubilizing agent based on at least one organotrisiloxane containing a polar function used is the mixture (M) prepared in Example 1

| Fragrance composition | |
|---|---|
| lavender | 7% by weight |
| mixture (M) | 93% |

This clear composition (solution) is obtained by simple mixing of its two constituents at room temperature.

EXAMPLE 3

| Fragrance composition | |
|---|---|
| lavender | 15% by weight |
| mixture (M) of Example 1 | 50% |
| hexamethyldisiloxane | 35% |

This clear composition (solution) is obtained by simple mixing of its three constituents at room temperature.

EXAMPLE 4

Fragrance compositions were prepared by simple mixing at room temperature of lavender according to the amounts given in the table below, and of the remainder to 100% by weight of one of the polyorganosiloxanes containing a polar or polarizable function, below:

- derivative of limonene and hydrogenoheptamethyltrisiloxane (A)
- derivative of α-methylstyrene dimer and hydrogenoheptamethyltrisiloxane (B)
- derivative of diethyl allyl malonate and hydrogenoheptamethyltrisiloxane (C)
- diphenyltetramethyldisiloxane PhSi(Me)$_2$—O—Si(Me)$_2$Ph (D)
- mixture (M)

and were compared with a fragrance composition comprising a non-polar and non-polarizable polyorganosiloxane derived from octene and hydrogenoheptamethyltrisiloxane (O).

| lavender % | 7.4 | 7 | 7 | 11 | 10 | 7 |
|---|---|---|---|---|---|---|
| polyorganosiloxane | (A) | (B) | (C) | (D) | (M) | (O) |
| appearance of the solution | L* | L* | L* | L* | L* | T** |

*L = clear
**T = turbid

It is found that, in contrast with the other polyorganosiloxanes, the polyorganosiloxane (O) does not make it possible to obtain a clear fragrance composition with lavender.

What is claimed is:

1. A clear fragrance composition comprising a fragrance base, said fragrance base being dissolved, and a lipophilic agent for dissolving said fragrance base, said lipophilic agent comprising phenylethylheptamethyltrisiloxane.

2. A Composition according to claim 1, wherein said solubilizing agent further comprising a mixture of heptamethyltrisiloxanes containing polarizable functions, said mixture comprising:
   - more than 70% by weight, of phenylethylheptamethyltrisiloxane of formula Me$_3$Si—O—Si(Me)(Z$^1$)—O—SiMe$_3$, wherein Z$^1$ represents the —CH$_2$—CH$_2$—Ph function,
   - less than 25% by weight, of trisiloxane of formula Me$_3$Si—O—Si(Me)(Z$^2$)—O—SiMe$_3$, wherein Z$^2$ represents the —CH(CH$_3$)—Ph function, and
   - less than 5% by weight, of trisiloxane of formula Me$_3$Si—O—Si(Me)(Z$^3$)—O—SiMe$_3$, in which Z$^3$ represents the —CH=CH—Ph function, wherein formula Me represents a methyl radical and Ph represents a phenyl radical.

3. A composition according to claim 2, wherein the mixture of heptamethyltrisiloxanes comprises:
   - at least 75% by weight, of phenylethylheptamethyltrisiloxane of formula Me$_3$Si—O—Si(Me)(Z$^1$)—O—SiMe$_3$,
   - from 10 to 20% by weight, of trisiloxane of formula Me$_3$Si—O—Si(Me)(Z$^2$)—O—SiMe$_3$, and
   - 0 to 2% by weight, of trisiloxane of formula Me$_3$Si—O—Si(Me)(Z$^3$)—O—SiMe$_3$.

4. A composition according to claim 1, comprising from about 3 to 20% of its weight of the fragrance base, and from about 75 to 97% of its weight of the solubilizing agent.

5. A composition according to claim 1, wherein the fragrance base is a perfume responsible for various perfume notes.

6. A composition according to claim 1, further comprising a volatile or non-volatile solvent for the fragrance base and having a weight ratio solubilizing agent/solvent of from about 5/95 to 95/5.

7. A composition according to claim 6, wherein the weight ratio is from about 10/90 to 90/10.

8. A composition according to claim 7, wherein the weight ratio is from about 25/75 to 90/10.

9. A composition according to claim 6, wherein the solvent is a volatile silicone solvent.

10. A composition according to claim 6, wherein the solvent is hexamethyldisiloxane, ethanol, or a mixture of hexamethyldisiloxane/ethanol.

11. A composition according to claim 1, comprising no alcohol.

12. A process for fragrancing a cosmetic formulation, comprising the step of adding a fragrancing amount of a composition as defined in claim 1, to said cosmetic formulation.

13. A process according to claim 12, wherein said phenylethylheptamethyltrisiloxane is an emollient for said fragrance composition.

14. A process according to claim 13, wherein said composition further comprises a solvent of the fragrance base.

15. A process according to claim 14, wherein the solvent is a volatile silicone solvent.

16. A process according to claim 14, wherein the solvent is hexamethyldisiloxane, ethanol, or a mixture of hexamethyldisiloxane/ethanol.

17. A process according to claim 14, wherein said composition comprises no alcohol.

18. A process according to claim 12, wherein said phenylethylheptamethyltrisiloxane is being used in a proportion of from 75 to 97% relative to the weight of said fragrance compositions containing from 3 to 20% of their weight of fragrance base.

19. A process for preparing a fragrance composition as defined in claim 1, comprising the step of dissolving said fragrance base with phenylethylheptamethyltrisiloxane.

20. A process according to claim 19, wherein said phenylethylheptamethyltrisiloxane, is used in a proportion of from 75 to 97% relative to the weight of said fragrance compositions containing from 3 to 20% of their weight of fragrance base.

* * * * *